United States Patent
Ullberg et al.

(10) Patent No.: US 8,467,496 B2
(45) Date of Patent: Jun. 18, 2013

(54) METHOD AND APPARATUS FOR MEASURING MOISTURE CONTENT IN A BIOLOGICAL MATERIAL

(75) Inventors: Anders Ullberg, Åby (SE); Ragnar Kullenberg, Oskarström (SE); Erik Odén, Täby (SE); Fredrik Danielsson, Ekerö (SE)

(73) Assignee: Mantex AB, Kista (SE)

( * ) Notice: Subject to any disclaimer, the term of this patent is extended or adjusted under 35 U.S.C. 154(b) by 308 days.

(21) Appl. No.: 12/998,226

(22) PCT Filed: Oct. 1, 2009

(86) PCT No.: PCT/EP2009/062767
§ 371 (c)(1), (2), (4) Date: Mar. 28, 2011

(87) PCT Pub. No.: WO2010/037820
PCT Pub. Date: Apr. 8, 2010

(65) Prior Publication Data
US 2011/0176658 A1    Jul. 21, 2011

(30) Foreign Application Priority Data
Oct. 2, 2008 (EP) .................................. 08165726

(51) Int. Cl.
*G01N 23/06* (2006.01)
(52) U.S. Cl.
USPC .......................................................... 378/53
(58) Field of Classification Search
USPC .......................................................... 378/53
See application file for complete search history.

(56) References Cited

U.S. PATENT DOCUMENTS

| | | | |
|---|---|---|---|
| 3,452,193 A | 6/1969 | Petersen | |
| 5,270,546 A | 12/1993 | Jamroz et al. | |
| 5,406,378 A | 4/1995 | Jamroz et al. | |
| 7,078,913 B1 | 7/2006 | Pelletier | |
| 2007/0137323 A1 | 6/2007 | Floyd et al. | |

FOREIGN PATENT DOCUMENTS

| | | |
|---|---|---|
| DE | 3034543 A1 | 4/1982 |
| EP | 0568460 A1 | 11/1993 |
| EP | 0568461 A1 | 11/1993 |
| EP | 1563917 A1 | 8/2005 |
| EP | 1801580 A2 | 6/2007 |
| GB | 111590 A | 6/1968 |
| WO | WO-9735175 A1 | 9/1997 |
| WO | WO-0101113 A1 | 1/2001 |

OTHER PUBLICATIONS

A. Nordell and K. J. Vikterlöf, *Measurements of moisture content in wood fuel with dual energy x-ray*, Värmeforsk Service AB, Apr. 2000, ISSN 0282-3772 (english language abstract and summary).

*Primary Examiner* — Courtney Thomas
(74) *Attorney, Agent, or Firm* — Harness, Dickey & Pierce, P.L.C.

(57) ABSTRACT

A method for measuring moisture content in a biological material in an automated procedure is disclosed. The method comprises the step of: providing a reference database for a plurality of different material types with known moisture content. Further, a sample of biological material, such as chips of wood, pulp, grain, crop or sugar canes, are scanned with electromagnetic radiation of at least two different energy levels and the amount of radiation transmitted through the sample of the biological material is determined at said two energy levels. Subsequently, a material type in the reference database most resembling the biological material of the biological material of the sample is identified, and the moisture content of the sample of biological material is determined based on the identified material type and the determined amounts of radiation transmitted through the sample.

15 Claims, 1 Drawing Sheet

METHOD AND APPARATUS FOR MEASURING MOISTURE CONTENT IN A BIOLOGICAL MATERIAL

TECHNICAL FIELD OF THE INVENTION

The present invention relates to a method and an apparatus for measuring the moisture content in a biological material in an automated procedure. The invention is particularly useful for measuring the moisture content in wood, such as wood chips.

BACKGROUND

In the wood industry it is of great importance to obtain precise measurements of the moisture content in the material to be processed, in order to achieve improved control of the process parameters. A precise knowledge of the relative amount of moisture content in the material is of a central importance for the quality of the end product in many processes within the wood and pulp industry. For example, it is advantageous to known in mechanical pulp processes whether the wood chips are fresh enough, i.e. having enough moisture content, to be able to be processable. Further, the optimal amount of chemicals to be added in the processes is dependent on the amount of fibers in the material, and in order to determine the amount of fibers it is necessary to correctly estimate the amount of moisture in the material.

Previously known methods to estimate the amount of fibers and moisture content in wood material involve drying of the material. However, such methods are cumbersome and tedious, and it would normally take a day or more until a correct measure value could be obtained, which delays the overall processing. It is therefore a need for a fast and reliable method to estimate the moisture content.

Similar needs exist in other industries handling biological material. For example, it would be advantageous to have a fast and reliable method for estimating the moisture content in the biological material in the bio energy field, in order to control the burning process more precisely, and improve its efficiency.

It is per se previously known to measure e.g. moisture content in wood using X-ray radiation. However, a common problem with such known methods is that that the apparatuses are large and expensive, that the methods are relatively tedious and cumbersome to perform, and/or that the results are imprecise and unreliable.

Further, the patent application WO 97/35175 by the same inventors discloses a method for using radiation of several energy levels in order to distinguish between e.g. different types of materials in wood, etc. However, this method requires additional measurement of the wood diameter, and is not adapted for e.g. moisture content estimations in automated processes.

Further, a very early example of use of X-ray for determining water-content in cellulosic sheets is disclosed in GB 1 115 904. However, the process discussed in this document is only to be used for thin sheets of material with known constituents, and is not suited for automatization. Still further, a paper titled "Measurement of moisture content in wood fuels with dual energy x-ray" by A. Nordell and K-J. Vikterlof, ISSN 0282-3772, discloses a similar approach for measuring moisture content in biofuels. However, also in this case the determination is based on prior knowledge of the material types and information related to this material type, and the process is neither intended nor suitable for an automated process.

There is therefore a need for a fast and accurate method and apparatus for estimating the moisture content in biological material, such as in wood, which can e.g. be used directly by people in field work operation, be used in automated processes, and the like.

SUMMARY OF THE INVENTION

It is therefore an object of the present invention to provide an improved method and apparatus for measuring the moisture content in a biological material in an automated process, which overcome or at least alleviate the above-discussed problems of the prior art.

This object is achieved by means of the invention as defined in the appended claims.

According to a first aspect of the invention there is provided a method for measuring moisture content in a biological material in an automated procedure, comprising the steps of:

providing a reference database for a plurality of different material types with known moisture content;

scan a sample of the biological material with electromagnetic radiation of at least two different energy levels;

determined the amount of radiation transmitted through said sample of the biological material at said two energy levels;

identify a material type in said reference database most resembling the biological material of the biological material of the sample; and determine the moisture content of said sample of biological material based on said identified material type and said determined amounts of radiation transmitted through the sample.

The present invention is particularly useable for estimating the moisture content in wood chips, but it may also be used for other forms of wood, as well as for other types of biological material, such as pulp, biomass fuel, etc. The invention is particularly useful for biological material in a liquid or separated form, and preferably in the form of chips. However, the invention is also useable for other types of biological material, and in particular different types of crop, such as corn, grain and sugar canes.

By "moisture content" is in this application meant the ratio between the quantity of moisture (i.e. water) in a certain quantity of material and the total material quantity. Consequently, estimation of moisture content in a material is also, indirectly, an estimation of the non-moisture content. In e.g. wood chips, the material essentially consist of moisture and fibers, and consequently, estimation of the moisture content is also in practice an estimation of the fiber content in the material. Similarly, the moisture content may, in accordance with the present invention, be estimated either directly, or indirectly by estimation of content of remaining constituents of the material.

The method of the present invention makes use of irradiation of two or more different energy levels, and determines the moisture content of the material, directly or indirectly, from the measured transmission energy, i.e. the amount of the radiation of each wavelength that is absorbed in the material. Different material types, such as different sort of wood, have different absorption coefficient. However, the inventive system compensates for this in a very effective way by using a reference database.

The irradiation of two or more different energy levels is preferably achieved by means of two or more radiation sources, such as two or more X-ray tubes. Preferably, the irradiation at each energy level derives from a separate radiation source. This is a relatively simple and cost-efficient solution, but yet very robust and reliable. Further, it enables the constant irradiation of the material, and irradiation of the same material with several wavelengths simultaneously, which makes it very useful e.g. for measuring of material being continuously transported past the measuring station.

Alternatively or additionally, the irradiation of two or more different energy levels is preferably detected by means of two or more detectors. Preferably, the irradiation at each energy level is detected in a separate radiation detector. This is a relatively simple and cost-efficient solution, but yet very robust and reliable. Further, it enables the constant irradiation of the material, and irradiation of the same material with several wavelengths simultaneously, which makes it very useful e.g. for measuring of material being continuously transported past the measuring station.

However, it is also possible to use a single radiation source emitting irradiation at different energy levels. This may e.g. be achieved by feeding the irradiation source with different voltage levels, e.g. by means of a high voltage switch, in order to provide intermittent irradiation with different energy levels. It is also possible to use e.g. k-edge filters in the radiation source in order to provide the different energy levels. Further, it is also possible to use a single detector capable of detecting irradiation at several energy levels, either consecutively or simultaneously.

The method/apparatus according to the present invention is very well suited for use in online measurements along conveyor lines where material is transported, in pipe-lines, on conveyor belts etc. This is possible, since e.g. the present invention can be used for various and varying heights and forms of the biological material, and without predetermined information about material type etc.

However, the present invention is also very useable for measuring samples of material arranged in sample containers, e.g. for sample testing in process industries, in the field measurements, etc.

Thus, the present invention may be used in fully or partly automated procedures, and requires no, or very limited, operator interaction.

The information regarding the biological material, in particular the identified material type and the determined moisture content, can then be used as input for the control of subsequent processing of the biological material. Hereby, the subsequent use of the biological material becomes more efficient. For example, this information could be used for obtaining more efficient purification, incineration, combustion, etc. The sending of this information to the control system and the use of said information for the control of the subsequent process may also be automated. Hereby, it is for example feasible to execute the identification of the material type and the determination of the moisture content in the biological material as it passes on its way into the subsequent procedure, and to control the process immediately based on said information. Thus, the subsequent process can hereby be controlled in real-time based on said information. However, it is also possible to store the information for later use in association with the specific sample or batch of biological material.

The radiation scan, which preferably comprises an X-ray radiation scan, also provides X-ray images that may be used for further analysis of the biological material. Thus, the detector signals may also be used for optical analysis, e.g. for determining the type of biological material that is at hand, and other properties of the material.

The data for the reference database is preferably assembled by measuring transmission of electromagnetic radiation of at least two different energy levels through a plurality of different material types, and by measuring the moisture content of said materials by means of a conventional method, and preferably by controlled drying. The material types may e.g. be different sorts of wood, such as birch, spruce, pine, oak, and alder. Hereby, the same type of measurement data as obtained with the subsequent measurement of new materials can be related to exactly measured moisture content data. Since the reference database needs only be created during the initialization, and can then be reused repeatedly, there is no particular need for speedy processes during these reference database measurements.

The amount of radiation transmitted through the sample of the biological material at the two energy levels is preferably determined in relation to a calibration reference value. The calibration reference value can e.g. be determined by measurement of the transmission of radiation through a reference material of a predetermined thickness, which is preferably made immediately before and/or after the each measurement through the biological material, the reference material e.g. being aluminum. Hereby, it is ensured that adequate calibration is always at hand.

A material type for the biological material is preferably identified in the reference database based on the determined amounts of radiation transmitted through the sample of the biological material at said two energy levels. In this way, the material type can be identified automatically, which makes the process very fast. However, it is also feasible to identify the material type in other ways, e.g. by input from an operator, by measurement of other parameters, such as color or density, etc. According to one alternative, an optical method may be used to determine the material type, e.g. based on the X-ray pictures provided through the detector. However, preferably the material type for the biological material is identified in the reference database as the material type having the most similar T-value, said T-value being calculated as:

$$T = \frac{(R_1 - \mu_{water1} * X_{water})}{(R_2 - \mu_{water2} * X_{water})}$$

wherein $R_1 = \ln(N_{01}/N_1)$, i.e the natural logarithm of the quotient between the calibrated reference value for the transmission $N_{01}$ and the transmission value through the biological material $N_1$ at a first energy level, and $R_2$ is the same quotient for a second energy level, $\mu_{water1}$ is an attenuation coefficient for water at the first energy level, $\mu_{water2}$ is the attenuation coefficient for water at the second energy level, and $X_{water}$ is an equivalent water thickness.

Further, the moisture content of the sample of biological material is preferably determined by determination of a K-value for the biological material, said K-value being calculated as:

$$K = \frac{\ln(N_{01}/N_1)}{\ln(N_{02}/N_2)}$$

wherein $N_{01}$, $N_{02}$ are the calibrated reference values for the transmission at the two energy levels and $N_1$, $N_2$ are the transmission values through the biological material at said energy levels, and estimation of the moisture content of said biological material by comparing said calculated K-value with corresponding K-values for the identified material type in said reference database. It has been found by the present inventors that the K-value is relatively linear for many types of biological material, in particular for many sorts of wood, and accordingly, relatively few specific values in the reference database for each type of biological material can still be used to provide accurate estimations of a broad range of moisture content values in the sample material. When the K-values are linearly dependent on the moisture content, it may even be sufficient to store only to different K-values in the reference database.

The scanning of the sample of the biological material with electromagnetic radiation of at least two different energy levels preferably comprises a first scan with a first energy level, and a subsequent second scan with a second energy level.

The at least two different energy levels are both preferably of X-ray radiation wavelengths. Further, the radiation of both said energy levels are preferably emitted from a single radiation source operating in the energy range 20-150 kVp. Here, kVp (Peak kilovoltage) denotes the maximum voltage applied across an X-ray tube. It determines the kinetic energy of the electrons accelerated in the X-ray tube and the peak energy of the X-ray emission spectrum. The actual voltage across the tube may fluctuate.

According to a second aspect of the invention, there is provided an apparatus for measuring moisture content in a biological material in an automated procedure, comprising:

a reference database comprising data for a plurality of different material types with known moisture content;

a scanning device for scanning a sample of the biological material with electromagnetic radiation of at least two different energy levels;

a detector for determining the amount of radiation transmitted through said sample of the biological material at said two energy levels; and a processor for identifying a material type in said reference database most resembling the biological material of the biological material of the sample, and determining the moisture content of said sample of biological material based on said identified material type and said determined amounts of radiation transmitted through the sample.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DETAILED DESCRIPTION OF PREFERRED EMBODIMENTS

Figure 1:
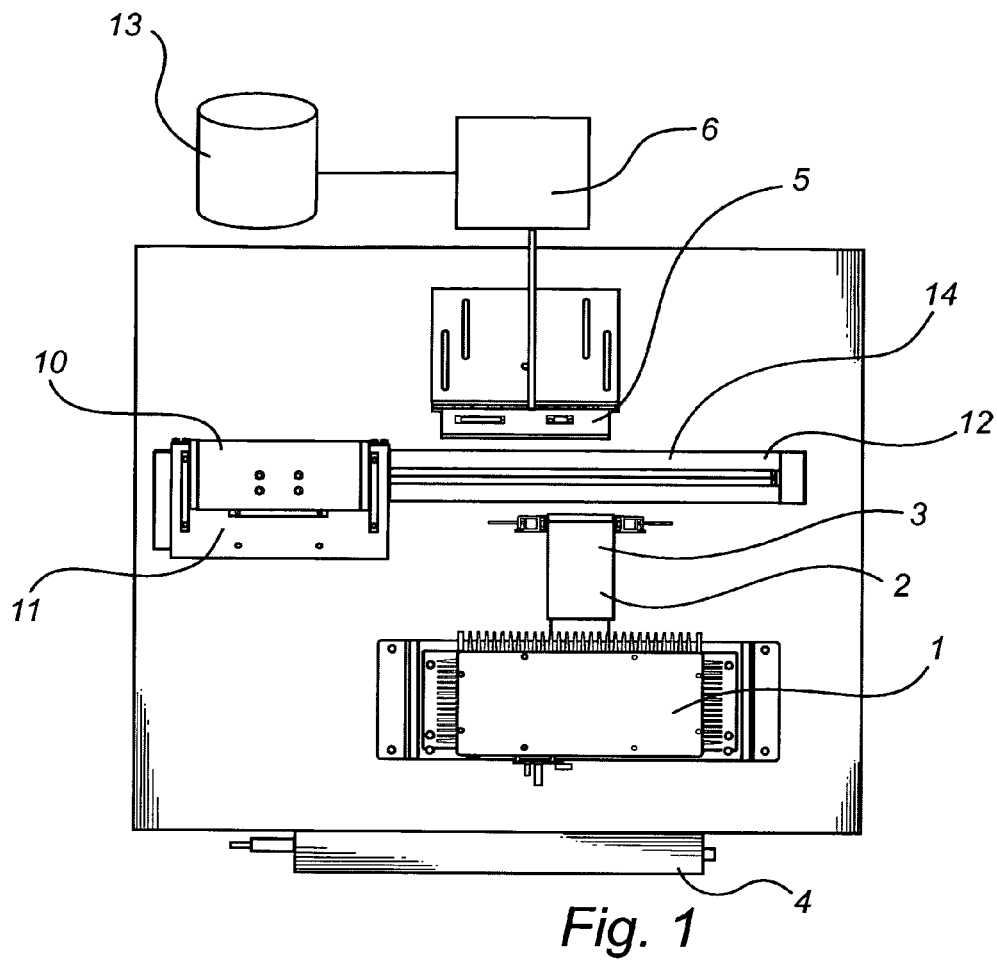
FIG. 1 is a schematic top view of a measurement apparatus according to an embodiment of the present invention.
Figure 2:
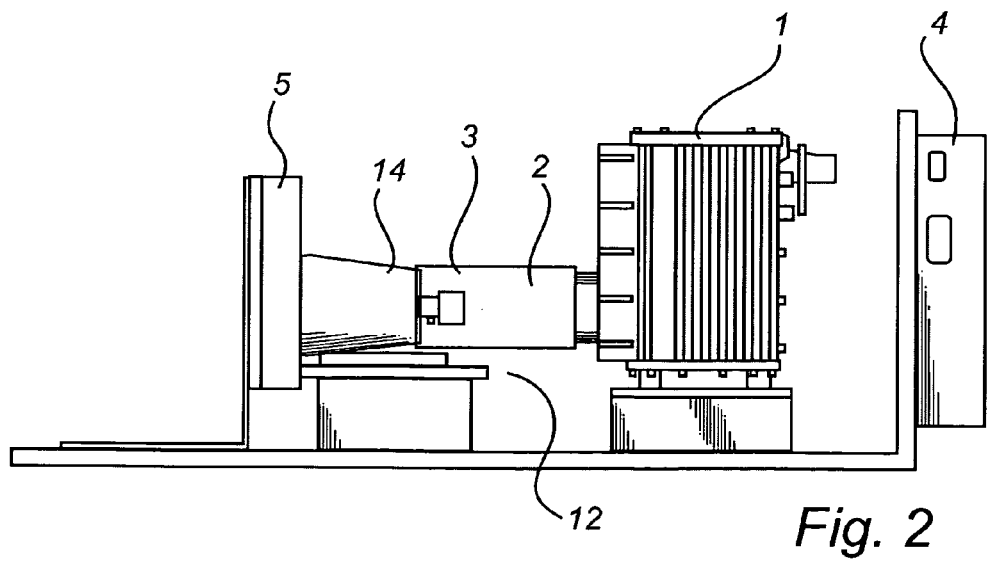
FIG. 2 is a simplified side view of the apparatus of claim 1, where some of the components of the apparatus as shown in FIG. 1 have been excluded for increased clarity.

Referring to FIGS. 1 and 2, an exemplary measurement apparatus according to the present invention comprises a radiation source 1 for providing radiation of at least two different energy levels/wavelengths. Preferably, the radiation source is an X-ray tube for provision of X-ray radiation of two or more different wavelengths. Preferably, the X-ray tube operates in the range 20-150 kVp. The output radiation from the radiation source is preferably directed towards a target area through a collimator 2 and a lens 3. The radiation source is controlled by means of a controller 4.

On the opposite side of the target area, a detector 5 is arranged to receive radiation transmitted through material arranged in the target area. The detector is preferably a semiconductor detector, comprising an array of semiconductor detector areas. The detector is connected to a control unit 6 with a processor, e.g. an ordinary personal computer. The control unit receives detection data from the detector through a suitable interface, such as through a USB port.

As would be obvious for any one skilled in the art, there are numerous alternatives for transporting material to be measured through the target area. In the disclosed embodiment, the material to be measured is arranged in a sample container 10. The sample container is arranged on a carrier 11, which is movable in such a way that the sample container is moved through the target area, and through the radiation path 14. The carrier may e.g. be moved by means of a conveyor 12. However, other means for moving the carrier are also feasible, such as linear motors, screw arrangements, rail arrangements and the like.

During operation, the material to be measured is scanned through the target area, and past the radiation source. At the first passage, the material sample is irradiated with radiation of a first wavelength, and in the second passage, during the return movement, with radiation of a second wavelength. In order to get a reference value for calibration, it is preferred to measure a reference material, and preferably a predetermined amount of aluminum, at the beginning and end of the passage of the sample container.

Based on these reference measurements, calibration reference values are determined as:

$$N_{O1,O2} = N_{Al1,2} \exp(\mu x)$$

where $N_{O1}$ and $N_{O2}$ are the calibration reference values for energy level 1 and 2, respectively, $N_{Al1}$ and $N_{Al2}$ are the detected transmission values after passage through the known thickness of aluminum, $\mu$ is the known attenuation coefficient for aluminum (cm$^{-1}$) and x is the known thickness of the aluminum (cm).

A reference database 13 is provided, connected to the control unit 6, with data concerning at least detected transmission values for the radiation at the different energy levels, and moisture content values, for different types of biological material, such as for a number of different sorts of wood.

Based on the detected transmission of radiation through the material to be tested at the different wavelengths, a material type for the biological material is identified in the reference database. Preferably, the material type for the biological material is identified in the reference database as the material type having the most similar T-value, said T-value being calculated as:

$$T = \frac{(R_1 - \mu_{water1} * X_{water})}{(R_2 - \mu_{water2} * X_{water})}$$

wherein $R_1 = \ln(N_{O1}/N_1)$, i.e the natural logarithm of the quotient between the calibrated reference value for the transmission $N_{O1}$ and the transmission value through the biological material $N_1$ at a first energy level, and $R_2$ is the same quotient for a second energy level, $\mu_{water1}$ is a linear attenuation coefficient for water at the first energy level, $\mu_{water2}$ is the linear attenuation coefficient for water at the second energy level, and $X_{water}$ an equivalent water thickness.

The equivalent water thickness may calculated as:

$$X_{water} = \frac{R_2 * \mu_{bio1} - R_1 * \mu_{bio2}}{\mu_{water2} * \mu_{bio1} - \mu_{water1} * \mu_{bio2}}$$

where $\mu_{bio1}$ is an attenuation coefficient for the biological material at the first energy level, and $\mu_{bio2}$ is the corresponding attenuation coefficient at the second energy level. The attenuation coefficients for the biological material need normally not be measured exactly, but is relatively predictable and can be based on an "educated guess" for any type of biological material.

Thereafter, the moisture content of the sample of biological material is determined by determination of a K-value for the biological material, said K-value being calculated as:

$$K = \frac{\ln(N_{01}/N_1)}{\ln(N_{02}/N_2)}$$

wherein $N_{01}$, $N_{02}$ are the calibrated reference values for the transmission at the two energy levels and $N_1$, $N_2$ are the transmission values through the biological material at said energy levels, and estimation of the moisture content of said biological material by comparing said calculated K-value with corresponding K-values for the identified material type in said reference database.

The matching of the K-value to K-values in the reference database may either be based on identification of the closest K-value identifiable in the reference database for the specific type of material at hand, and using the corresponding moisture value as the estimate for the sample. A correction may also be used in order to compensate for the difference between the actual K-value and the identified closest K-value in the reference database.

Alternatively, the K-values for the specific material type may be used in a linear or polynomial representation of the correspondence between the K-value and the moisture content, and this function may then be used for an estimate of the moisture content corresponding to the K-value of the sample material.

Specific embodiments of the invention have now been described. However, several alternatives are possible, as would be apparent for someone skilled in the art. For example, the radiation need not be X-ray, but other types of electromagnetic radiation may also be used. Further, there are various ways of determining the type of biological material, both automatically and semi-automatically. Depending on the intended line of use, the reference database can be customized to comprise only the most probable material types, or comprise a large variety of different material types. Still further, the implementation of the control and processing method could be accomplished in different ways, such as in especially dedicated hardware or in software for control of already existing control means.

Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A method for measuring moisture content in a biological material in an automated procedure, comprising the steps of:
providing a reference database for a plurality of different material types with known moisture content;
scanning a sample of the biological material with electromagnetic radiation of at least two different energy levels;
determining the amount of radiation transmitted through said sample of the biological material at said two energy levels;
identifying a material type in said reference database most resembling the biological material of the biological material of the sample; and
determining the moisture content of said sample of biological material based on said identified material type and said determined amounts of radiation transmitted through the sample.

2. The method of claim 1, wherein the data for the reference database is assembled by measuring transmission of electromagnetic radiation of at least two different energy levels through a plurality of different material types, and by measuring the moisture content of said materials by means of a conventional method, and preferably by controlled drying.

3. The method of claim 1, wherein the scanning of a sample of the biological material with electromagnetic radiation of at least two different energy levels comprises arranging the biological material in a separated form, and preferably in the form of chips.

4. The method of claim 3, wherein the scanning of the sample of the biological material with electromagnetic radiation of at least two different energy levels comprises arranging the biological material in a sample container.

5. The method of claim 1, wherein the amount of radiation transmitted through the sample of the biological material at said two energy levels is determined in relation to a calibration reference value.

6. The method of claim 5, wherein the calibration reference value is determined by measurement of the transmission of radiation through a reference material of a predetermined thickness, said calibration measurement preferably being made immediately before and/or after the each measurement through the biological material, the reference material preferably being aluminum.

7. The method of claim 1, wherein a material type for the biological material is identified in said reference database based on the determined amounts of radiation transmitted through said sample of the biological material at said two energy levels.

8. The method of claim 7, wherein the material type for the biological material is identified in said reference database as the material type having the most similar T-value, said T-value being calculated as:

$$T = \frac{(R_1 - \mu_{water1} * X_{water})}{(R_2 - \mu_{water2} * X_{water})}$$

wherein $R_1 = \ln(N_{01}/N_1)$, i.e the natural logarithm of the quotient between the calibrated reference value for the transmission $N_{01}$ and the transmission value through the biological material $N_1$ at a first energy level, and $R_2$ is the same quotient for a second energy level, $\mu_{water1}$ is an attenuation coefficient for water at the first energy level, $\mu_{water2}$ is the attenuation coefficient for water at the second energy level, and $X_{water}$ is an equivalent water thickness.

9. The method of claim 1, wherein the moisture content of said sample of biological material is determined by determination of a K-value for said biological material, said K-value being calculated as:

$$K = \frac{\ln(N_{01}/N_1)}{\ln(N_{02}/N_2)}$$

wherein $N_{O1}$, $N_{O2}$ are the calibrated reference values for the transmission at the two energy levels and $N_1$, $N_2$ are the transmission values through the biological material at said energy levels, and estimation of the moisture content of said biological material by comparing said calculated K-value with corresponding K-values for the identified material type in said reference database.

10. The method of claim 1, wherein the scanning of the sample of the biological material with electromagnetic radiation of at least two different energy levels comprises a first scan with a first energy level, and a subsequent second scan with a second energy level.

11. The method of claim 1, wherein the at least two different energy levels both are of X-ray radiation wavelengths.

12. The method of claim 1, wherein the radiation of both said energy levels are emitted from a single radiation source operating in the energy range 20-150 kVp.

13. An apparatus for measuring moisture content in a biological material in an automated procedure, comprising:
- a reference database comprising data for a plurality of different material types with known moisture content;
- a scanning device for scanning a sample of the biological material with electromagnetic radiation of at least two different energy levels;
- a detector for determining the amount of radiation transmitted through said sample of the biological material at said two energy levels; and
- a processor for identifying a material type in said reference database most resembling the biological material of the biological material of the sample, and determining the moisture content of said sample of biological material based on said identified material type and said determined amounts of radiation transmitted through the sample.

14. The apparatus of claim 13, further comprising at least two radiation sources for generation of the at least two different energy levels, and preferably at least one radiation source for each specific energy level.

15. The apparatus of claim 13, wherein there is provided at least two detectors for determining the amount of radiation transmitted through said sample of the biological material at said two energy levels, and preferably at least one detector for each specific energy level.

* * * * *